(12) United States Patent
Pereira et al.

(10) Patent No.: US 10,390,922 B2
(45) Date of Patent: Aug. 27, 2019

(54) DEVICES AND METHODS FOR DELIVERY OF ATTACHMENT DEVICES

(71) Applicant: Boston Scientific Scimed, Inc., Maple Grove, MN (US)

(72) Inventors: Peter J Pereira, Mendon, MA (US); Rebecca DeLegge, Mount Pleasant, SC (US); Lauren Eskew, Mount Pleasant, SC (US)

(73) Assignee: Boston Scientific Scimed, Inc., Maple Grove, MI (US)

( * ) Notice: Subject to any disclaimer, the term of this patent is extended or adjusted under 35 U.S.C. 154(b) by 194 days.

(21) Appl. No.: 14/987,047

(22) Filed: Jan. 4, 2016

(65) Prior Publication Data

US 2016/0193023 A1    Jul. 7, 2016

Related U.S. Application Data

(60) Provisional application No. 62/099,824, filed on Jan. 5, 2015.

(51) Int. Cl.
*A61F 2/00* (2006.01)
*A61B 17/06* (2006.01)
(Continued)

(52) U.S. Cl.
CPC ...... *A61F 2/0022* (2013.01); *A61B 17/00234* (2013.01); *A61B 17/0401* (2013.01);
(Continued)

(58) Field of Classification Search
CPC ............. A61F 2/0022; A61B 17/06066; A61B 17/06061; A61B 2017/0608; A61B 17/00234; A61B 17/0401; A61B 17/06109; A61B 17/42; A61B 2017/00867; A61B 2017/0417; A61B 2017/0419; A61B 2017/0448; A61B 2017/0458
See application file for complete search history.

(56) References Cited

U.S. PATENT DOCUMENTS 5,820,628 A    10/1998  Middleman et al.
5,972,005 A *  10/1999  Stalker ............... A61B 17/0057
                                                      606/144

(Continued)

OTHER PUBLICATIONS

International Preliminary Report on Patentability for PCT Application No. PCT/US2016/012191, dated Jul. 20, 2017, 11 pages.
(Continued)

*Primary Examiner* — Christine H Matthews
*Assistant Examiner* — Joshua Daryl D Lannu
(74) *Attorney, Agent, or Firm* — Brake Hughes Bellermann LLP

(57) ABSTRACT

In a generic aspect, an apparatus for delivering attachment devices includes a needle defining a lumen and a distal opening, and a plurality of attachment devices disposed within the lumen of the needle. Each attachment device includes a first attachment part, a second attachment part, and a connecting member coupled to the first attachment part and the second attachment part. The apparatus further includes an actuator configured to drive each attachment device out of the distal opening of the needle during a surgical procedure.

19 Claims, 10 Drawing Sheets

(51) Int. Cl.
*A61B 17/00* (2006.01)
*A61B 17/04* (2006.01)
*A61B 17/42* (2006.01)

(52) U.S. Cl.
CPC .. *A61B 17/06061* (2013.01); *A61B 17/06066* (2013.01); *A61B 17/06109* (2013.01); *A61B 17/42* (2013.01); *A61B 2017/00867* (2013.01); *A61B 2017/0417* (2013.01); *A61B 2017/0419* (2013.01); *A61B 2017/0448* (2013.01); *A61B 2017/0458* (2013.01); *A61B 2017/0608* (2013.01)

(56) References Cited

U.S. PATENT DOCUMENTS

| | | |
|---|---|---|
| 6,626,919 B1 | 9/2003 | Swanstrom |
| 6,669,707 B1 | 12/2003 | Swanstrom et al. |
| 2004/0225305 A1* | 11/2004 | Ewers ............... A61B 1/00135 606/153 |
| 2005/0251177 A1 | 11/2005 | Saadat et al. |
| 2007/0112425 A1 | 5/2007 | Schaller et al. |

OTHER PUBLICATIONS

International Search Report and Written Opinion for PCT Application No. PCT/US2016/012191, dated Aug. 1, 2016, 17 Pages.
Invitation to Pay Add'l Fees and Partial Search Report for PCT Application No. PCT/US2016/012191, dated May 4, 2016, 8 pages.

* cited by examiner

DEVICES AND METHODS FOR DELIVERY OF ATTACHMENT DEVICES

CROSS-REFERENCE TO RELATED APPLICATION

This application is a Nonprovisional of, and claims priority to, U.S. Patent Application No. 62/099,824, filed on Jan. 5, 2015, entitled "DEVICES AND METHODS FOR DELIVERY OF ATTACHMENT DEVICES", which is incorporated by reference herein in its entirety.

TECHNICAL FIELD

This disclosure relates generally to delivery devices and surgical procedures, and particularly delivery devices and methods used for delivering attachment devices.

BACKGROUND

Pelvic organ prolapse is an abnormal descent or herniation of the pelvic organs. A prolapse may occur when muscles and tissues in the pelvic region become weak and can no longer hold the pelvic organs in place correctly. Treatment for symptoms of the pelvic organ prolapse can include changes in diet, weigh control, and lifestyle. Treatment may also include surgery, medications, and the use of implants (e.g., graphs) to support the pelvic organs. Sacrocolpopexy is a surgical technique that may be used to repair pelvic organ prolapse. Sacrocolpopexy may be performed using an open abdominal technique or with the use of minimally invasive surgery, such as laparoscopy or robotic-assisted surgery.

The Sacrocolpopexy technique may use an implant to be inserted into the body. For example, multiple sutures are used to attach the implant to both sides of the vaginal wall as well as the sacral ligament. During the procedure, sometimes 12-16 sutures are thrown and tied, which can be very time consuming. Increased surgical time may lead to infection and a poor recovery rate.

SUMMARY

In a generic aspect, an apparatus for delivering attachment devices includes a needle defining a lumen and a distal opening, and a plurality of attachment devices disposed within the lumen of the needle. Each attachment device includes a first attachment part, a second attachment part, and a connecting member coupled to the first attachment part and the second attachment part. The apparatus further includes an actuator configured to drive each attachment device out of the distal opening of the needle during a surgical procedure.

The apparatus may include one or more of the following features (or any combination thereof). The needle may include a shape memory material. The connecting member may be a suture. The actuator may drive the first attachment part to a first location, and the second attachment part to a second location, where the first location and the second location are located on a same side of a tissue layer. The actuator may be a pusher wire. Each of the first attachment part and the second attachment part may separately define a lumen and a reduced-diameter lumen. The first attachment part may define a lumen and a side slot, and the second attachment part may define a lumen and a side slot. The first attachment part may be identical to the second attachment part. The first attachment part may be disposed adjacent to the second attachment part with the connecting member being housed within a lumen of the first and second attachment parts. The plurality of attachment devices may be serially disposed within the needle's lumen. Each of the first attachment part and the second attachment part may include a coupling member configured to couple an end portion of the connecting member.

According to a generic aspect, a method for delivering attachment devices in a body of a patient includes loading an attachment device in a lumen of a needle. The attachment device includes a first attachment part, a second attachment part, and a connecting member coupled to the first attachment part and the second attachment part. The method includes moving the needle through an entry point such that the needle curves back to a first location, where the first location is located on a same side as the entry point. The method further includes releasing the first attachment part via a distal opening of the needle, manipulating the needle such that a distal tip of the needle is moved to a second location proximate to the entry point, and releasing the second attachment part via the distal opening of the needle.

The method may include one or more of the following features (or any combination thereof). Each of the first attachment part and the second attachment part may define a lumen and a reduced-diameter lumen. The connecting member may include a stopper on a first end portion of the connecting member and a stopper on a second end portion of the connection member. The diameter of the reduced-diameter lumen of the first and second attachment parts may be smaller than the stopper's diameter. The manipulating the needle may include retracting the needle into a needle carrier such that the needle is forced to a linear configuration. In some examples, the tissue is a vaginal wall, and a distal tip of the needle does not completely go through the vaginal wall during movement of the needle.

According to a generic aspect, an apparatus for delivering attachment devices includes a needle defining a lumen and a distal opening, and a plurality of attachment devices disposed within the lumen of the needle. Each attachment device includes a first attachment part, a second attachment part, and a connecting member coupled to the first attachment part and the second attachment part. The apparatus further includes an actuator configured to drive each attachment device out of the distal opening of the needle during a surgical procedure.

The apparatus may include one or more of the following features (or any combination thereof). The needle may include a shape memory material. The needle may include a shape memory material. The connecting member may be a suture. The actuator may drive the first attachment part to a first location, and the second attachment part to a second location. The first location and the second location may be located on the same side of a tissue layer. The actuator may be a pusher wire. The first attachment part may define a lumen and a side slot, and the second attachment part may define a lumen and a side slot. The first attachment part may be disposed adjacent to the second attachment part with the connecting member being housed within a lumen of the first and second attachment parts. The plurality of attachment devices may be serially disposed within the lumen of the needle. Each of the first attachment part and the second attachment part may include a coupling member configured to couple an end portion of the connecting member.

According to a generic aspect, an apparatus for delivering attachment devices includes a needle carrier, and a needle configured to move to a first position and a second position in relation to the needle carrier. The needle has a curved portion when in the second position. The needle is substantially linear in the first position. The needle defines a lumen and a distal opening. The apparatus further includes a plurality of attachment devices serially disposed within the lumen, and an actuator configured to drive the attachment devices through the lumen and out of the distal opening in either the first position or the second position.

The apparatus may include one or more of the following features (or any combination thereof). The needle carrier may define a lumen configured to receive at least a portion of the needle such that the portion of the needle moves from the first position in which the portion of the needle is retracted within the needle carrier to the second position in which the portion of the needle extends from a distal end of the needle carrier. Each of the attachment devices may include a first attachment part, a second attachment part, and a connecting member coupled to the first attachment part and the second attachment part. The needle may include a shape memory material that is biased to a curved configuration forming the curved portion. The curved portion may be J-shaped. In some examples, the actuator is a pusher wire, and the apparatus further includes a handle operatively coupled to the pusher wire, where manipulation of the handle distally moves the pusher wire to drive the attachment devices towards the distal opening of the needle.

According to a generic aspect, a method for delivering attachment devices in a body of a patient includes loading an attachment device in a lumen of a needle. The attachment device includes a first attachment part, a second attachment part, and a connecting member coupled to the first attachment part and the second attachment part. The method further includes moving the needle into tissue at an entry point, and moving the needle through the tissue such that the needle curves back to a first location. The first location is located on the same side of tissue as the entry point. The method further includes releasing the first attachment part via a distal opening of the needle, manipulating the needle such that a distal tip of the needle is moved back through the tissue to a second location proximate to the entry point, and releasing the second attachment part via the distal opening of the needle.

The method may include one or more of the following features (or any combination thereof). Each of the first attachment part and the second attachment part may define a lumen and a reduced-diameter lumen. The connecting member may include a stopper on a first end portion of the connecting member and a stopper on a second end portion of the connecting member. The diameter of the reduced-diameter lumen is smaller than the stopper's diameter. The manipulating the needle may include retracting the needle into a needle carrier such that the needle is forced to a linear configuration. In some examples, the tissue is a vaginal wall.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are to medical devices, methods of making medical devices, and procedures for placing medical devices within a body of a patient. The term patient may hereafter be used for a person who benefits from the medical device or the methods disclosed in the present application. For example, the patient can be a person whose body is operated through the medical device or the method disclosed by the present invention. For example, in some embodiments, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1A:
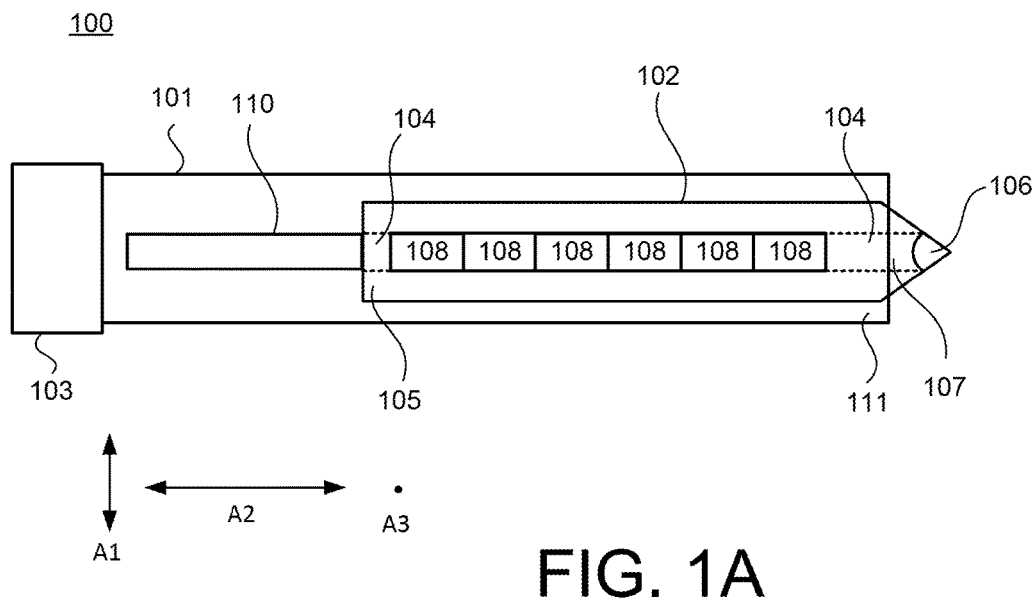
FIG. 1A illustrates a delivery device having a needle in a retracted position in relation to a needle carrier.
Figure 1B:
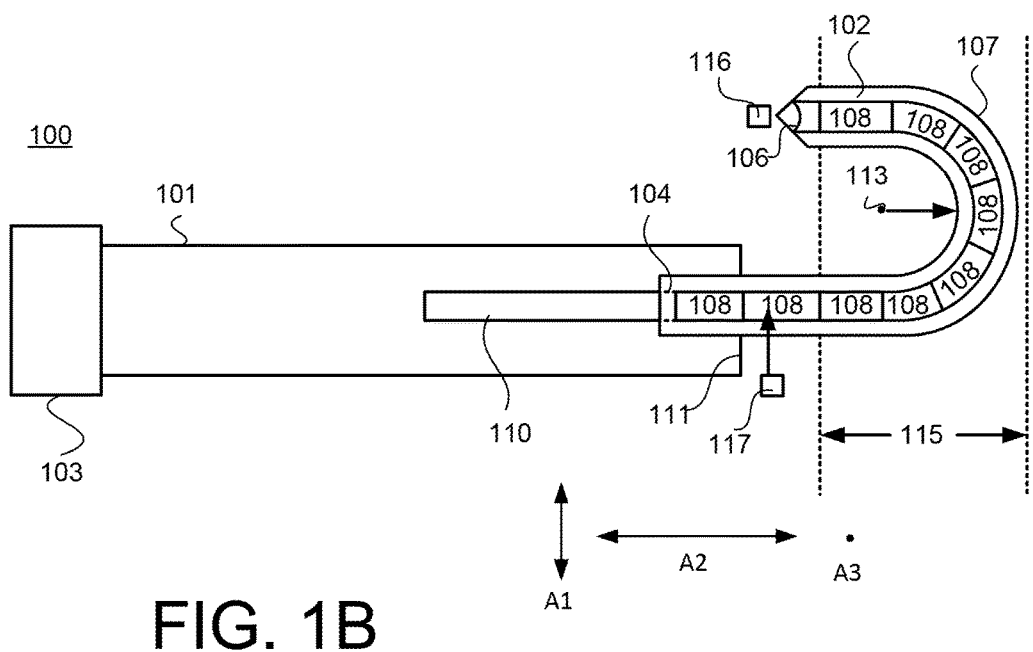
FIG. 1B illustrates the needle of the delivery device in an extended position in relation to the needle carrier.
Figure 1C:
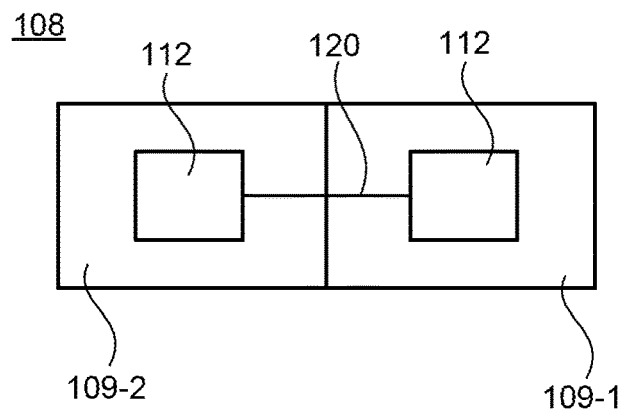
FIG. 1C illustrates an attachment device having a first attachment part stacked with a second attachment part.
Figure 1D:
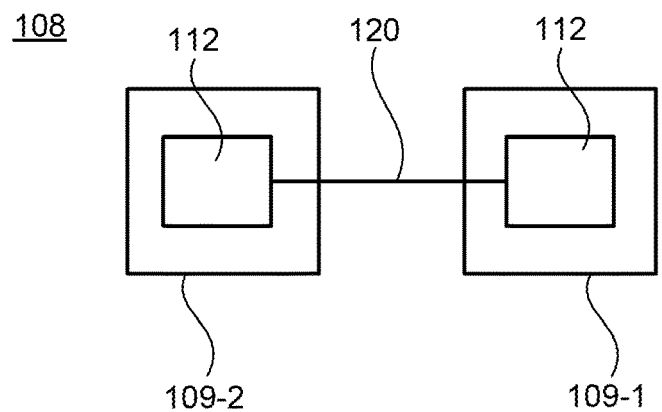
FIG. 1D illustrates a deployed attachment device.

FIGS. 1A-1B are schematic diagrams of a delivery device 100 having a needle 102 configured to hold and deliver attachment devices 108 into a body of the patient. In some examples, the needle 102 is a hollow shape memory needle having a pre-set curved shape but can bend to a linear shape. Each attachment device 108 may couple two pieces of tissue together or couple an implant to bodily tissue (e.g., vaginal mesh to vaginal tissue). FIGS. 1C-1D are schematic diagrams of the attachment devices 108. Each attachment device 108 includes a first attachment part 109-1, a second attachment part 109-2, and a connecting member 120 coupled to the first attachment part 109-1 and the second attachment part 109-2.

As shown in FIG. 1C, the attachment parts 109-1 and 109-2 are stacked adjacent to each other with the connecting member 120 being enclosed within a structure (e.g., lumen, cavity, slot, etc.) of the attachment parts 109-1 and 109-2, thereby creating a stackable unit which can be stacked with other attachment devices 108 within the needle 102. Referring to FIG. 1B, when the needle 102 is driven forward and released from its trapped state, the needle 102 forms a curved portion 107. Also, an actuator 110 may be configured to drive the attachment devices 108 out of the needle 102 such that a single attachment device 108 is released from the needle 102 part-by-part (e.g., the first attachment part 109-1 is deployed followed by the second attachment part 109-2). Further, the radius of curvature of the needle 102 may be sufficiently low such that the distal tip of the needle 102 curves back to the same surface from which it entered.

The delivery device 100 may be a medical device used in a surgical procedure. The surgical procedure may be a sacrocolpopexy that is used to repair pelvic organ prolapse. During the sacrocolpopexy, an implant is inserted into the body, and multiple sutures are used to attach the implant to both sides of the vaginal wall as well as the sacral ligament. During the procedure, sometimes 12-16 sutures are thrown and tied, which can be very time consuming. However, according to some embodiments, the delivery device 100 may be configured to dispense multiple attachment devices 108 in a manner that decreases surgical time by providing a multi-fire mechanism that allows multiple throws without having to re-load or remove the delivery device 100 out of the body of the patient. In addition, in some embodiments, the delivery device 100 allows the user to enter in and out of the patient's tissue without changing the angles or pinching the tissue, as further discussed below.

The delivery device 100 may include a needle carrier 101 configured to hold the needle 102. The needle carrier 101 may be an elongate member part of a laparascopic device. The needle carrier 101 may be a shaft. The needle carrier 101 may be a piece of outer tubing. The needle carrier 101 may define a lumen configured to receive the needle 102. In some examples, the delivery device 100 may include a handle 103. The handle 103 may be operatively coupled to the actuator 110 such that manipulation of the handle 103 causes the actuator 110 to drive the attachment devices 108 through the needle 102. In other examples, the actuator 110 is triggered by a component other than the handle 103.

The needle 102 may be constructed from a shape memory material. The shape memory material may be any type of material having the ability to return to an original state. In some examples, the shape memory material is nitinol. The original state may be the curved configuration, as shown in FIG. 1B. For example, when in the original state (or relaxed state), the needle 102 curves forming the curved portion 107. The curved portion 107 may be in two or three dimensional planes. In some examples, the needle 102 curves into a J-shape. However, the needle 102 may deform into other shapes when pressure is applied to the needle 102. When pressure is removed, the needle 102 returns to its original state.

The needle 102 may move in relation to the needle carrier 101 along an axis A2 between a first position (as shown in FIG. 1A) and a second position (as shown in FIG. 1B), as well as any position between the first position and the second position. For example, a user may operate the delivery device 100 so that the needle 102 is moved along the axis A2 in the distal direction. The axis A2 may be parallel to a longitudinal axis of the delivery device 100. An axis A1 may be perpendicular to the axis A2. An axis A3 into the page (shown as a dot) is orthogonal to the axes A1 and A2. The axes A1, A2, and A3 are used throughout several of the various views of the implementations described throughout the figures for simplicity.

The first position may be a retracted position such that most (or all) of the needle 102 is disposed within the lumen defined by the needle carrier 101. FIG. 1A illustrates the needle 102 in the retracted position such that the needle 102 (or a portion thereof) is trapped within the needle carrier 101. In the retracted position, the needle 102 has a substantially linear configuration (e.g., the needle 102 is not curved or is devoid of curved portions). The second position may be an extended position such that a portion of the needle 102 extends beyond the distal end 111 of the needle carrier 101. FIG. 1B illustrates the needle 102 in the extended position. In the extended position, the needle 102 has the curved configuration. As the needle 102 extends out of the needle carrier 101, the needle 102 reverts to its pre-defined shape, e.g., forming the curved portion 107. In some examples, the curved portion 107 of the needle 102 is less than the entire length of the needle 102. In some examples, the curved portion 107 of the needle 102 is a distal end portion of the needle 102.

The curved portion 107 defines a radius of curvature 113. The radius of curvature 113 may be relatively small such that the distal tip of the needle 102 reflects back on the same surface of tissue. For example, the radius of curvature 113 of the needle 102 may be designed such that the user may enter and exit out of the tissue on the same surface without changing the angles or pinching the tissue. The radius of curvature 113 may be defined below a threshold level such when the needle 102 extends into the vaginal wall, the distal tip curves around to the same surface from which it entered without going completely through the vaginal wall, as further explained below.

In some embodiments, the needle 102 is configured to enclose an attachment device 108. In some embodiments, the needle 102 is configured to enclose a plurality of attachment devices 108. The needle 102 defines an internal lumen 104 that extends a length of the needle 102. The needle 102 may be hollow. The needle 102 may be cylindrical or tubular defining an inner diameter and an outer diameter, where the inner diameter defines the internal lumen 104. In other examples, the needle 102 has a non-cylindrical shape such as square, rectangular, or D-shaped. The internal lumen 104 may be circular or tubular. In other examples, the internal lumen 104 may have a non-cylindrical shape. The internal lumen 104 may have a shape that corresponds to the shape of the needle 102 (e.g., if the needle 102 is cylindrical, the internal lumen 104 is cylindrical). In other examples, the internal lumen 104 may have a shape that is different to the shape of the needle 102. The internal lumen 104 may be linear. In other examples, the internal lumen 104 has one or more curved regions. The needle 102 may define a distal opening 106 on a distal end portion of the needle 102. The distal opening 106 is in communication with the internal lumen 104. Although not shown in FIGS. 1A-1D, the needle 102 may have a proximal opening that is on the other end of the needle 102. The needle 102 may be configured to pierce bodily tissue. In some examples, the distal tip of the needle 102 may be sharp. In other examples, the distal tip of the needle 102 may be blunt.

The attachment devices 108 may be stacked within the internal lumen 104 of the needle 102. The attachment devices 108 may be serially disposed within the internal lumen 104. For example, each attachment device 108 may be disposed adjacent to another attachment device 108 within the internal lumen 104 of the needle 102. Also, the attachment devices 108 may be relatively flexible such that the needle 102 can curve to its pre-defined curved shape while holding the attachment devices 108 within the internal lumen 104, as shown in FIG. 1B.

The actuator 110 is configured to drive the attachment devices 108 out of the internal lumen 104 via the distal opening 106. The actuator 110 may be a pusher component that pushes the attachment devices 108 through the internal lumen 104 of the needle 102. The actuator 110 may be a pusher wire. The actuator 110 may operate in conjunction with a user-operated component (e.g., trigger, button, lever, plunger, etc.). In some examples, the handle 103 causes the actuator to move the attachment devices 108. For example, the user may be able to squeeze the handle 103 thereby driving the actuator 110 into the internal lumen 104 to push the attachment devices 108.

The user may trigger the actuator 110 to sequentially release the attachment devices 108 part-by-part. In other words, each activation causes a pre-defined movement of the actuator 110 such that the attachment devices 108 are discharged part-by-part. For example, each activation may incrementally push the attachment devices 108 through the internal lumen 104. A first activation may cause one-half of a single attachment device 108 (e.g., the first attachment part 109-1) to be discharged via the distal opening 106, and a second activation may cause the other-half of the attachment device 108 (e.g., the second attachment part 109-2) to be discharged via the distal opening 106. Further activations cause the other attachment devices 108 to be released in the same manner until no more attachment devices 108 are left within the internal lumen 104 of the needle 102. As such, the delivery device 100 may be configured to dispense multiple attachment devices 108 in a manner that may decrease surgical time by providing a multi-fire mechanism that allows multiple throws without having to re-load or remove the delivery device 100 out of the body of the patient.

Referring to FIGS. 1C-1D, each attachment device 108 includes the first attachment part 109-1, the second attachment part 109-2, and the connecting member 120 coupled to the first attachment part 109-1 to the second attachment part 109-2. Each of the attachment parts 109-1 and 109-2 may be any type of attachment component capable of attaching to an implant or body tissue. In some examples, the attachment parts 109-1 and 109-2 are anchors. The attachment device 108 may be configured to couple two pieces of tissue together. For example, the first attachment part 109-1 is configured to be coupled to bodily tissue, and the second attachment part 109-2 is configured to be coupled to bodily tissue. In some examples, the attachment device 108 is configured to couple the implant to bodily tissue. For example, the first attachment part 109-1 is configured to be coupled to the implant, and the second attachment part 109-2 is configured to be coupled to bodily tissue. In some examples, the first and second attachment parts 109-1, 109-2 can be configured to be coupled to a mesh and tissue simultaneously.

The second attachment part 109-2 has a structure that is identical to the first attachment part 109-1. In other examples, the structure of the second attachment part 109-2 is different to the first attachment part 109-1. Generally, the first and second attachment parts 109-1, 109-2 include structures that correspond to the internal lumen 104 of the needle 102. In some examples, each of the attachment parts 109-1 and 109-2 is a tubular member. In some examples, each of the attachment parts 109-1 and 109-2 is a T-shaped member. For example, each of the attachment parts 109-1 and 109-2 may define a hollow tube with an opening down half of its length, which allows the connecting member 120 to lie within the lumen of the tube within the stacked configuration, but can be pulled out of that opening when deployed.

The connecting member 120 may be a flexible elongate member configured to couple the attachment parts 109-1 and 109-2 together, where one portion of the connecting member 120 is coupled to the first attachment part 109-1 and another portion of the connecting member 120 is coupled to the second attachment part 109-2. In some examples, the connecting member 120 is a suture. In some examples, the connecting member 120 is an elastic member. The connecting member 120 may have a length such that, when extended, the second attachment part 109-2 is connected to but separated by a distance from the first attachment part 109-1. The connecting member 120 may have a stopper disposed each end portion of the connecting member 120. In some examples, the stopper is a knot formed by tying the connecting member 120. In other examples, the stopper is a bead or other component configured to engage each of the attachment parts 109-1 and 109-2.

Each of the attachment parts 109-1 and 109-2 includes a coupling component 112 configured to couple a portion of the connecting member 120. The coupling component 112 of the first attachment part 109-1 may couple a first end portion of the connecting member 120 to the first attachment part 109-1, and the coupling component 112 of the second attachment part 109-2 may couple a second end portion of the connecting member 120 to the second attachment part 109-2. In some examples, the coupling component 112 may be a reduced-diameter section of the attachment part 109-1 or 109-2. For example, one end portion of the connecting member 120 may be tied into a knot (stopper), and the knot may be disposed on one side of the reduced-diameter section. The knot may be larger than a diameter of the reduced-diameter section such that the engagement of the knot to the reduced-diameter section prevents the connecting member 120 from being decoupled from each of the attachment parts 109-1 and 109-2. In other examples, the coupling component 112 is a part separate from the attachment part 109-1 or 109-2, but is coupled to the attachment part 109-1 or 109-2 in order to couple a portion of the connecting member 120 to the attachment part 109-1 or 109-2. However, the coupling component 112 may be any type of structure, component, or mechanism that can couple the connecting member 120 to the attachment part 109-1 or 109-2. Also, the connecting member 120 may be molded, fused, melted, or glued to the first attachment part 109-1 and the second attachment part 109-2.

FIG. 1C illustrates the attachment device 108 with the first attachment part 109-1 disposed adjacent to the second attachment part 109-2 such that the connecting member 120 is housed within the stacked attachment parts 109-1 and 109-2. As shown in FIG. 1C, the first attachment part 109-1 is engaged with the second attachment part 109-2 with the connecting member 120 being housed within the lumen of the attachment device 108. For example, the first attachment part 109-1 and the second attachment part 109-2 may define a lumen, slot, or cavity that is capable of housing portions of the connecting member 120. As such, when the second attachment part 109-2 is stacked adjacent to the first attachment part 109-1, the adjacent attachment parts 109 at least partially surround the connecting member 120. As such, the design of the attachment parts 109-1 and 109-2 permits the connecting member 120 to be housed within the adjacent attachment parts 109-1 and 109-2, thereby creating a stackable unit that allows multiple attachment devices 108 to be serially stacked next to each other within the internal lumen 104 of the needle 102.

FIG. 1D illustrates a deployed attachment device 108 having the first attachment part 109-1 connected to the second attachment part 109-2 via the connecting member 120. For example, the connecting member 120 may have a length such that the second attachment part 109-2 may be disposed a distance from the first attachment part 109-1. However, the connecting member 120 is sufficiently flexible so that when the first attachment part 109-1 is engaged with the second attachment part 109-2 (as shown in FIG. 1C), the connecting member 120 may compact such that it fits within the housing of the attachment parts 109-1 and 109-2.

Referring to FIG. 1B, in one example which couples vaginal tissue to an implant, the needle 102 may be inserted through the implant, and then inserted into the vaginal wall 115 or tissue proximate the vaginal wall at an entry point. Then, the needle 102 may be extended such that it curves around to the same surface from which it entered in a manner that the needle 102 does not completely go through the vaginal wall 115. The actuator 110 may be triggered such that the first attachment part 109-1 of the attachment device 108 is deployed at a first location 116. For example, the actuator 110 advances the attachment devices 108 through the internal lumen 104, where the first attachment part 109-1 is pushed out of the distal opening 106 of the needle 102 at the first location 116. Then, the needle 102 may be retracted back into the needle carrier 101 such that the distal tip is moved proximate to the entry point of the vaginal wall or tissue proximate the vaginal wall. For example, the needle 102 is retracted back into the needle carrier 101 in a curved motion such that the needle 102 does not completely go through the vaginal wall 115 until the distal tip of the needle 102 is proximate to the entry point. Then, the actuator 110 is triggered such that the second attachment part 109-2 of the attachment device 108 is deployed at a second location 117. A shown in FIG. 1B, the first location 116 and the second location 117 is on the same side of tissue. The curvature of the needle 102 in conjunction with the delivery mechanism of the delivery device 100 allows the user the ability to go in and out of the vaginal tissue on the same surface without changing the angles or pinching the tissue. Further, the needle 102 does not completely through the vaginal wall 115, but rather curved around to the same surface from which it entered. However, it is noted that the delivery device 100 may be used in conjunction with any type of tissue besides vaginal tissue.

FIGS. 2A-2D illustrate various perspectives of a delivery device 200 having a needle 202 configured to house and deploy a plurality of attachment devices 208. In some examples, the needle 202 is a hollow shape memory needle that is bendable such that at least a portion can form a curved portion 207 when in its normal relaxed state, but is substantially straight when disposed within the delivery device 200. The delivery device 200 may include any of the features discussed with reference to the delivery device 100 of FIG. 1.

Each attachment device 208 includes a first attachment part 209-1, a second attachment part 209-2, and a connecting member 220 connected to the first attachment part 209-1 to the second attachment part 209-2. Each of the attachment parts 209-1 and 209-2 may be any type of attachment component capable of attaching to an implant or body tissue. In some examples, each of the attachment part 109-1 and 109-2 is an anchor. The attachment device 208 may be configured to couple two pieces of tissue together. In some examples, the attachment device 208 is configured to couple the implant to bodily tissue.

Figure 2A:
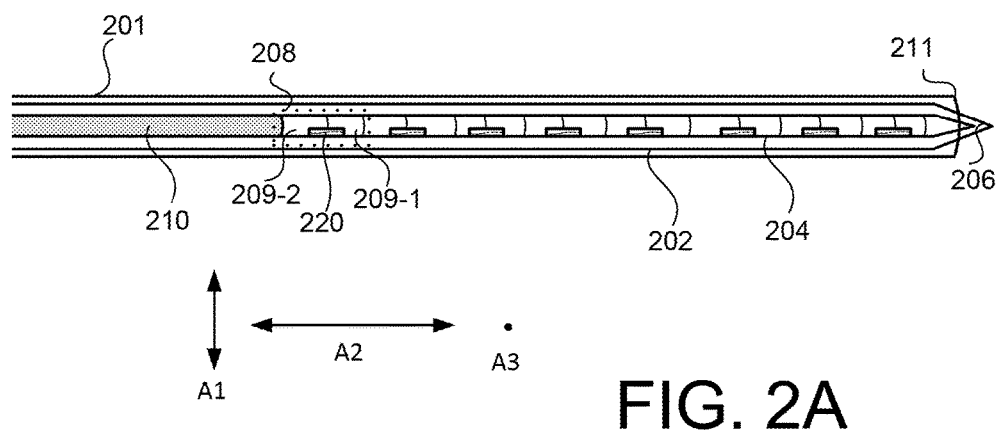
FIG. 2A illustrates a delivery device in a retracted position in relation to a needle carrier.
Figure 2B:
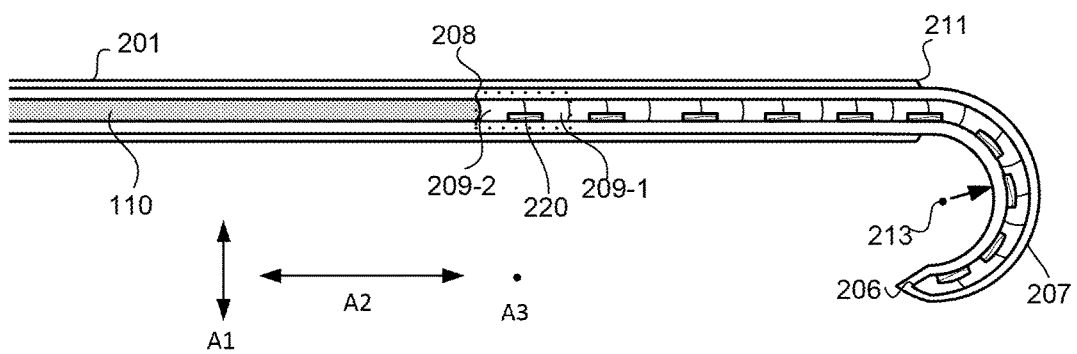
FIG. 2B illustrates the delivery device in an extended position in relation to the needle carrier.

Referring to FIG. 2A, the needle 202 is within the retracted position in relation to the delivery device 200. The needle 202 defines an internal lumen 204 configured to hold the attachment devices 208. The attachment devices 208 may be serially stacked within the internal lumen 204 of the needle 202. The delivery device 200 may include a needle carrier 201 configured to hold the needle 202 and permit the needle 202 to move from the retracted position (FIG. 2A) to the extended position (FIG. 2B). In some examples, the needle carrier 201 is a piece of outer tubing. In other examples, the needle carrier 201 is part of a larger device, e.g., a laparoscopic device. The needle carrier 201 may define a lumen configured to receive portions of the needle 202. In the retracted position, the distal tip of the needle 202 protrudes and is advanced from a distal end 211 of the needle carrier 201, but most of the needle 202 is disposed within the needle carrier 201. In the retracted position, the needle 202 has a substantially linear configuration, but the distal tip of the needle 202 protrudes from the needle carrier 201 in order to pierce bodily tissue as the delivery device 200 is inserted into the body of the patient.

Referring to FIG. 2B, the needle 202 is distally moved in relation to the needle carrier 201 until the needle 202 is in the extended position. For example, the needle 202 may slide out of the needle carrier 201. In some examples, only a portion of the needle 202 slides out of the needle carrier 201. In some examples, a majority of the needle 202 slides out of the needle carrier 201. The needle 202 may move along the axis A2 in the distal direction while the needle carrier 201 remains relatively stationary. As the needle 202 slides out or is advanced in relation to the needle carrier 201, the needle 202 reverts to its biased shape, e.g., curved or J-shaped configuration.

The needle 202 may be constructed from a shape memory material. The shape memory material may be any type of material having the ability to return to an original state. In some examples, the shape memory material is nitinol. The original state may be the curved configuration, as shown in FIG. 2B. For example, when in the original state (or relaxed state), the needle 202 curves forming the curved portion 207.

As shown in FIG. 2B, the attachment devices 208 are at least partially flexible such that they may conform to the curvature of the curved portion 207 of the needle 202. In some examples, the curved portion 207 may have a radius of curvature 213. The radius of curvature 213 may be relatively small such that the distal tip of the needle 202 reflects back on the same surface of tissue. As such, the curvature of the needle 202 may be designed such that the user may enter and exit out of the tissue on the same surface without changing the angles or pinching the tissue. In some examples, the radius of curvature 213 is less than 5 mm. In some examples, the radius of curvature is between 2 mm and 5 mm. In some examples, the radius of curvature is between 3 mm and 5 mm. In some examples, the radius of curvature is greater than 5 mm.

Figure 2C:
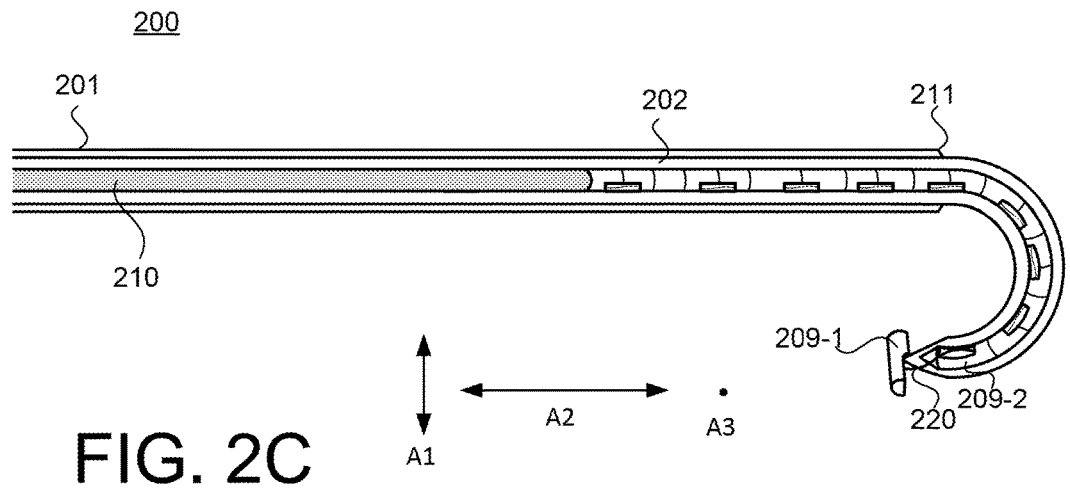
FIG. 2C illustrates a first attachment part deployed from a distal opening of the needle.

Referring to FIG. 2C, the user may trigger an actuator 210 to push the first attachment part 209-1 out of the needle 202 via its distal opening 206. For example, the user may deploy one-half of the attachment device 208 when the needle 202 is in the extended position. In some examples, the actuator 210 is a pusher component such as a pusher wire. As such, the user may trigger movement of the pusher wire in the distal direction, thereby pushing the attachment devices 208 as a whole until the first attachment part 209-1 for the attachment device 208 that is closest to the distal opening 206 of the needle 202 is released.

Figure 2D:
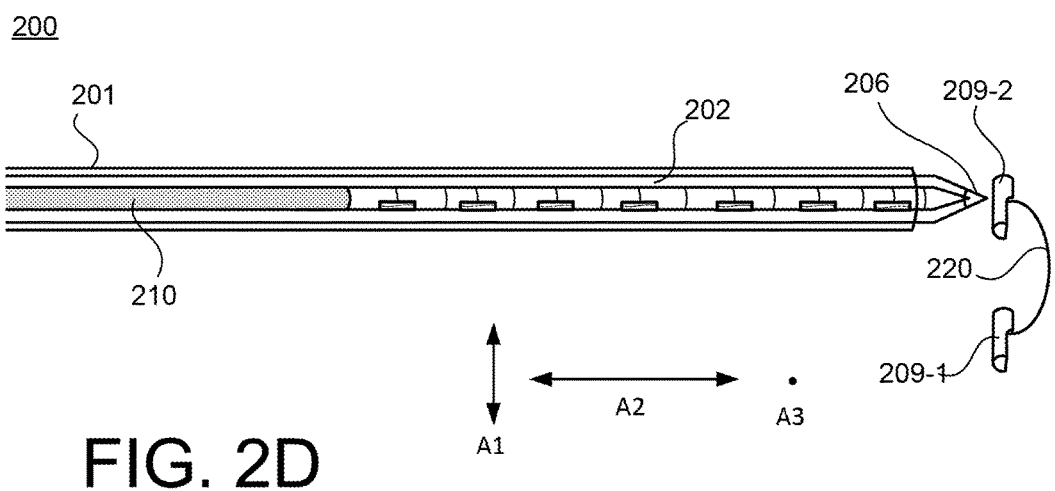
FIG. 2D illustrates a second attachment part deployed from the distal opening of the needle.

As shown in FIG. 2D, the needle 202 may be moved back to its retracted position. For example, the needle 202 may slide back into the needle carrier 201 such that the distal tip of the needle 202 is moved to the same side of tissue which it entered. Then, the user may trigger the actuator 210 to push the second attachment part 209-2 out of the needle 202 via its distal opening 206. In some examples, the user may trigger movement of the pusher wire in the distal direction, thereby pushing the attachment devices 208 as a whole until the second attachment part 209-2 is released. Then, the delivery device 200 may be placed in another location, and the process repeated for another attachment device 208. In this manner, the delivery device 200 may be configured to dispense multiple attachment devices 208 in a manner that decreases surgical time by providing a multi-fire mechanism that allows multiple throws without having to re-load or remove the delivery device 200 out of the body of the patient.

Figure 3A:
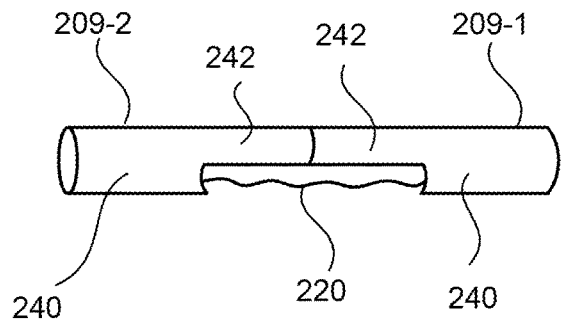
FIG. 3A illustrates the first attachment part engaged with the second attachment part with a connecting member disposed within the attachment part's housing.
Figure 3B:
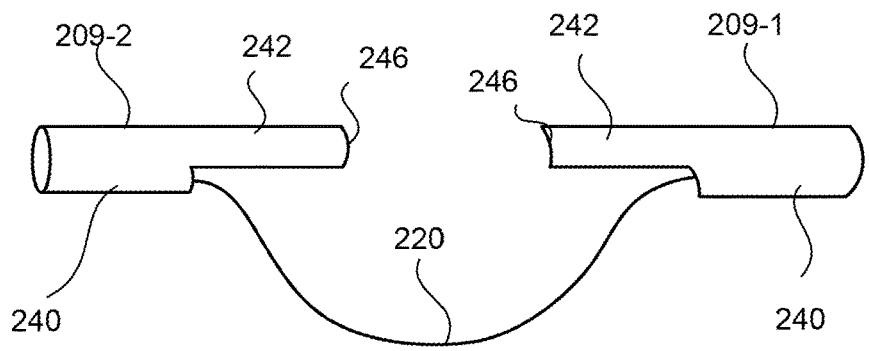
FIG. 3B illustrates a deployed attachment device.
Figure 3C:
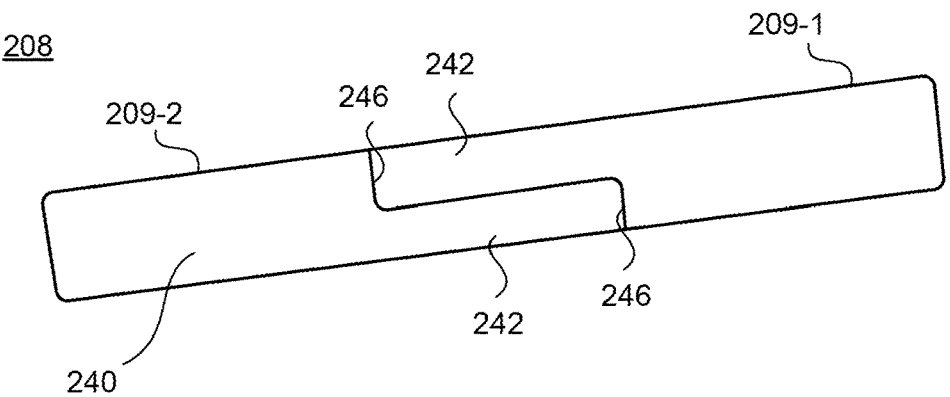
FIG. 3C illustrates the first attachment part and the second attachment part in another configuration.

FIGS. 3A-3C illustrate perspectives of the attachment device 208 having the first attachment part 209-1 connected to the second attachment part 209-2 via the connecting member 220. FIG. 3A illustrates the first attachment part 209-1 engaged with the second attachment part 209-2 with the connecting member 220 disposed within the attachment part's housing. The first attachment part 209-1 may be identical to the second attachment part 209-2, as illustrated with respect to FIG. 3C. In some examples, the attachment device 208 may be considered a T-unit (e.g., the attachment parts 209-1 and 209-2 and the connecting member 220 together forming the T).

The first attachment part 209-1 may be a unitary component having a fully circular member or portion 240 and a partially circular member or portion 242. For example, the fully circular member 240 may be a tubular member having a cross-section that forms a complete loop. The fully circular member 240 may define an internal lumen. The connecting member 220 may be coupled to the fully circular member 240 from the inside of the fully circular member 240. The partially circular member 242 may be a tubular member having a cross-section that forms a partially circular loop (e.g., does not form a complete loop). In some examples, the partially circular member 242 may be u-shaped. Stated another way, the partially circular member 242 may be a tube structure with a portion removed or a tube structure that includes or defines a slot. The partially circular member 242 may include an inner curved portion 246 configured to engage with the inner curved portion 246 of the other attachment part 209 when the attachment device 208 is within the internal lumen 204 of the needle 202. The inner curved portion 246 may be convex. In other examples, as shown in FIG. 3C, the first attachment part 209-1 may be turned upside down with respect to an orientation of the second attachment part 209-2 such that the connecting member 220 is fully enclosed (e.g., the inner curved portions 246 engaging the fully circular members 240).

Figure 4:
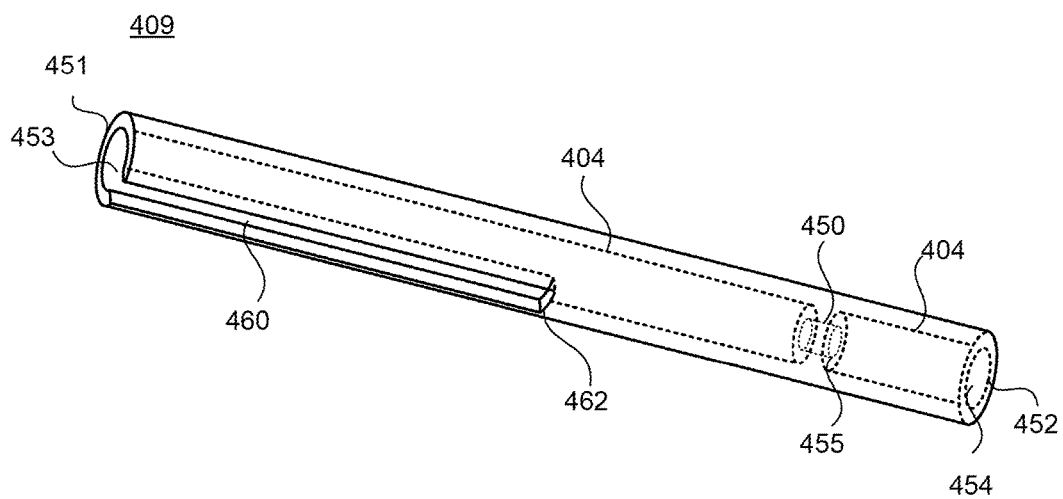
FIG. 4 illustrates a perspective of an attachment part.
Figure 6:
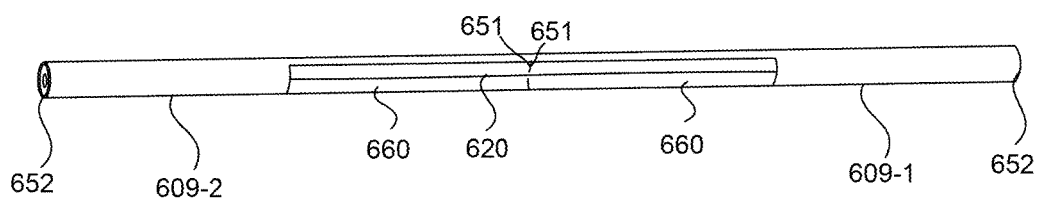
FIG. 6 illustrates stacked attachment parts forming a stackable unit configured to move through the needle.

FIG. 4 illustrates a perspective of an attachment part 409. The attachment part 409 may be used within any of the delivery devices discussed here. The attachment part 409 includes a reduced-diameter lumen 450 to secure a connecting member (e.g., connecting member 120/220) to its structure. The following description for the attachment part 409 applies to both attachment parts of an attachment device, e.g., a first attachment part stacked with a second attachment part. For instance, the attachment part 409 is one half of an overall attachment device. As such, the attachment part 409 may be stacked within another attachment part 409 to form a stackable unit. An example of stacked attachment parts are shown in FIG. 6. The attachment part 409 may define a lumen having multiple sizes. Stated another way, the attachment part 409 may provide a diameter change to secure a knot of the connecting member to the attachment part 409 such that the attachment part 409 can house the connecting member when stacked with another attachment part 409. In other examples, instead of using a knot, the connecting member (e.g., suture) includes an attachment or bulbous material. For example, the attachment part 409 may provide an area to deposit an adhesive (e.g., glue) such that a suture can be melted on one end to create a bulb.

For example, attachment part 409 may define a lumen 404 and the reduced-diameter lumen 450. The reduced-diameter lumen 450 may have a diameter smaller than the diameter of the lumen 404. The reduced-diameter lumen 450 may be located at a point along the lumen 404. In some examples, the reduced-diameter lumen 450 may be located towards a second end 452 of the attachment part 409 that is away from a first end 451 that engages with the other attachment part 409. The intersection of the reduced-diameter lumen 450 and the lumen 404 may define a shoulder 455. In some examples, the shoulder 455 may be non-tapered (e.g., flat). In other examples, the shoulder 455 may be tapered.

The connecting member may include a knot. In other examples, the connecting member may include a bead or other component that operates as a stopper. The connecting member may extend within the lumen 404 and the reduced-diameter lumen 450 with the stopper disposed on one side of the reduced-diameter lumen 450. The stopper includes a size larger than the diameter of the reduced-diameter lumen 450 such that the connecting member is prevented from moving in one of the directions.

The attachment part 409 may be a tubular member defining a first opening 453 on the first end 451 of the attachment part 409 and a second opening 454 on the second end 452 of the attachment part 409. The first end 451 is configured to engage with the first end 451 of the other attachment part 409. Each second end 452 of the attachment part 409 may be considered the outer ends of the attachment device. The stopper of the connecting member may be disposed on the side of the reduced-diameter lumen 450 proximate to the second end 452. As such, in some examples, the stopper is configured to engage with the shoulder 455 to prevent the connecting member from being decoupled from the attachment part 409.

The attachment part 409 may define a side slot 460 that extends from the first opening 453 to a location 462 at a middle portion of the attachment part 409. In some examples, the side slot 460 has a length that is one half of the length of the attachment part 409. The portion of the attachment part 409 having the side slot 460 may be considered the partially circular member 242 of FIG. 3A-3B. The portion of the attachment part 409 without having the side slot 440 may be considered the fully circular member 240 of FIGS. 3A-3B. After the attachment part 409 is released or deployed, portions of the connecting member may exit out of the side slot 460.

Figure 5:
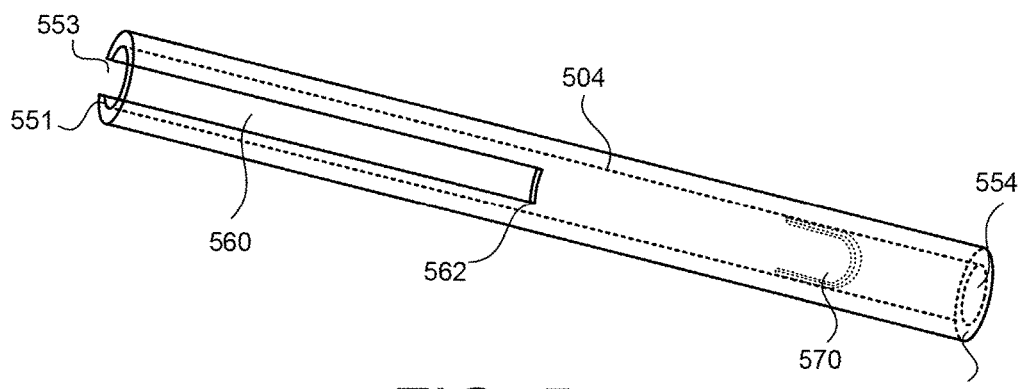
FIG. 5 illustrates another perspective of an attachment part.

FIG. 5 illustrates a perspective of an attachment part 509. For example, the attachment part 509 includes a swaged point 570 to secure a connecting member to its structure. For example, the attachment part 509 of FIG. 5 is substantially the same as the attachment part 409 except that the swaged point 570 is used instead of the reduced-diameter lumen 450 for coupling the connection member. The swaged point 570 may be a u-shaped member that is disposed within the lumen to trap the suture against the side of the lumen.

The attachment part 509 may be a tubular member defining a first opening 553 on a first end 551 of the attachment part 509 and a second opening 554 on the second end 552 of the attachment part 509. The first end 551 is configured to engage with the first end 551 of the other attachment part 509. Each second end 552 of the attachment part 509 may be considered the outer ends of the attachment device. The attachment part 509 may define a side slot 560 that extends from the first opening 553 to a location 562 at a middle portion of the attachment part 509. In some examples, the side slot 560 has a length that is one half of the length of the attachment part 509. The stopper of the connecting member may be disposed on the side of the swaged point 570 proximate to the second end 552. As such, in some examples, the stopper is configured to engage with a portion of the inner surface of the attachment part 509 to prevent the connecting member from being decoupled from the attachment part 509.

FIG. 6 illustrates stacked attachment parts 609-1 and 609-2 that form a stackable unit configured to move through a needle. For example, an attachment device includes a first attachment part 609-1, a second attachment part 609-2, and a connecting member 620 coupled to the first attachment part 609-1 and the second attachment part 609-2. The attachment part 609-1 or 609-2 may be any of the attachment parts described with reference to the previous figures. In some examples, the first attachment part 609-1 is identical to the second attachment part 609-2.

As explained above, each of the attachment parts 609-1 and 609-2 include a first end 651 and a second end 652. The first end 651 may be considered an inner portion. For example, the first end 651 of the first attachment part 609-1 may engage with the first end of the second attachment part 609-2. The second end 652 of the first attachment part 609-1 and the second end 652 of the second attachment part 609-2 may be considered the outer portions. Each of the attachment parts 609-1 and 609-2 defines a side slot 660. In some examples, the side slot 660 has a length that is one half of the length of the attachment part 609-1 or 609-2. As shown in FIG. 6, a stackable unit is formed by engaging the first attachment part 609-1 with the second attachment part 609-2 such that the connecting member 620 is housed within the attachment parts 609-1 and 609-2.

Figure 7:
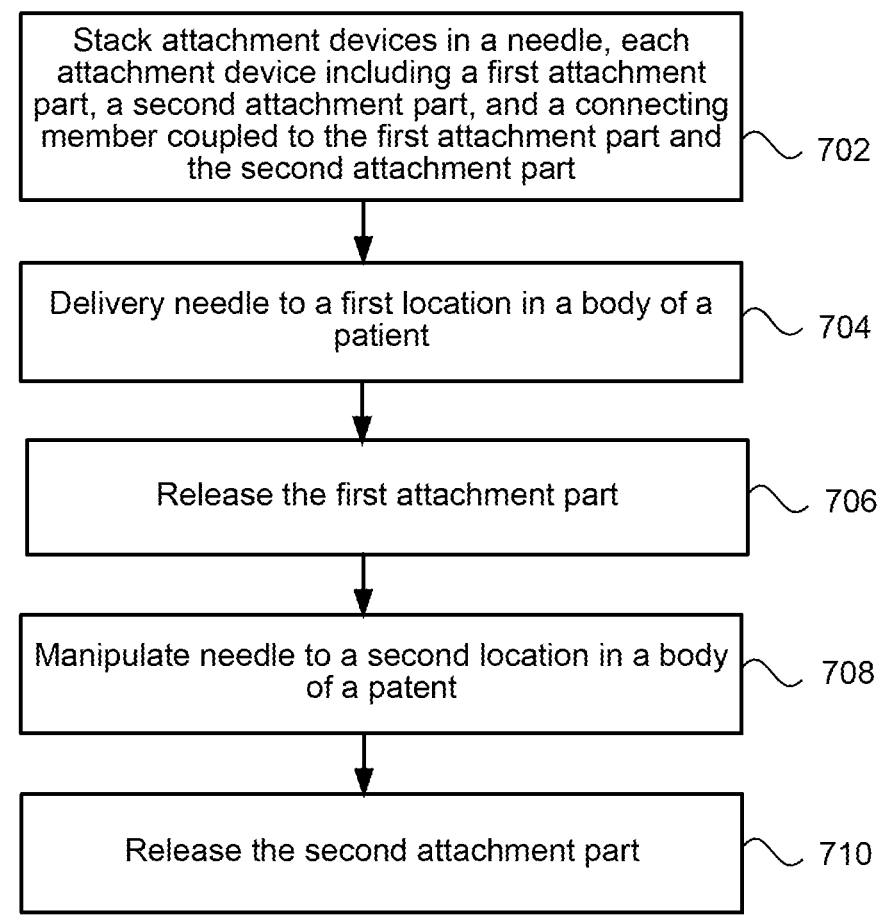
FIG. 7 is a flow chart for a method of delivering attachment devices into a body of a patient.

FIG. 7 is a flow chart for a method 700 of delivering attachment devices into a body of a patient according to an aspect. The method 700 may be applied to any type of surgical procedure that delivers attachment devices to couple bodily tissue together or couple bodily tissue to an implant. In some examples, the surgical procedure is a sacrocolpopexy. The sacrocolpopexy procedure may be performed using an open abdominal technique or with the use of minimally invasive surgery, such as laparoscopy or robotic-assisted surgery.

Attachment devices may be stacked in a needle (702). Each attachment device may include a first attachment part, a second attachment part, and a connecting member coupled to the first attachment part and the second attachment part. The first attachment part may be identical and separate from the second attachment part. In some examples, the first and second attachment parts may define a lumen. In some examples, the first and second attachment parts may define a slide slot. The needle may define a lumen, and the attachment devices may be inserted into the lumen of the needle. The first and second attachment parts may define a coupling member configured to couple each end portion of the connecting member. In some examples, the connecting member is a suture. In some examples, the coupling member is a reduced-diameter lumen. In some examples, the coupling member is a swaged-point. In some examples, the needle may include a shape memory material.

Needle may be delivered to a first location in a body of a patient (704). In some examples, the needle may be inserted through an implant, and then into a layer of tissue at an entry point such that the needle curves around to the same side in which it entered. In some examples, the layer of tissue is a vaginal wall. In some examples, the needle curves around to the same side of tissue in which it entered such that the needle does not go entirely through the vaginal tissue. The needle may be extended out of a needle carrier, and the needle may revert back to its original shape, e.g., curved configuration. In some examples, the curved configuration may be a J-shape.

The first attachment part may be released (706). For example, an actuator may be triggered to drive the attachment devices within the lumen of the needle until the first attachment part is discharged from a distal opening of the needle. In some examples, the actuator may be a pusher wire operatively coupled to a user-operated component. In some examples, the user may squeeze a handle, thereby moving the pusher wire a pre-set distance, which is sufficient to push the first attachment part out of its distal opening.

Needle may be manipulated to a second location in a body of the patient (708). In some examples, the needle may be retracted in relation to the needle carrier such that the distal tip of the needle is pulled to the same side of tissue in which it entered, which is proximate to the entry point.

The second attachment part may be released (710). For example, the actuator may be triggered to drive the attachment devices within the lumen of the needle until the second attachment part is discharged from the distal opening of the needle. In some examples, the actuator may be the pusher wire operatively coupled to a user-operated component. In some examples, the user may squeeze a handle, thereby moving the pusher wire a pre-set distance, which is sufficient to push the second attachment part out of its distal opening.

Figure 8:
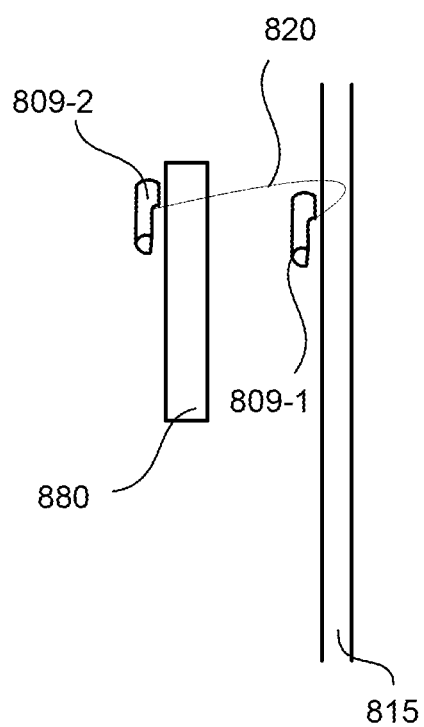
FIG. 8 illustrates an implant coupled to tissue of a vaginal wall using an attachment device.

FIG. 8 illustrates an implant 880 coupled to tissue of a vaginal wall 815 using an attachment device, as described in the method 700 of FIG. 7. Also, it is noted that although one attachment device is shown in FIG. 8, the steps of FIG. 7 may be repeated to attach the implant 880 to the vaginal wall 815 with multiple attachment devices. The attachment device includes a first attachment device 809-1, a second attachment device 809-2, and a connecting member 820. The first attachment part 809-1 may be the first attachment part 109-1, 209-1, 409, 509, 609-1, or 909-1 described with reference to any of the figures. The second attachment part 809-2 may be the second attachment part 109-2, 209-2, 409, 509, 609-2, and 909-2 described with reference to any of the figures. The connecting member 820 may be the connecting member 120, 220, 620, or 920 described with reference to any of the figures. The implant 880 may be any type of implant used for treating pelvic organ prolapse. The implant 880 may be a mesh implant having any type of size and/or configuration.

Figure 9:
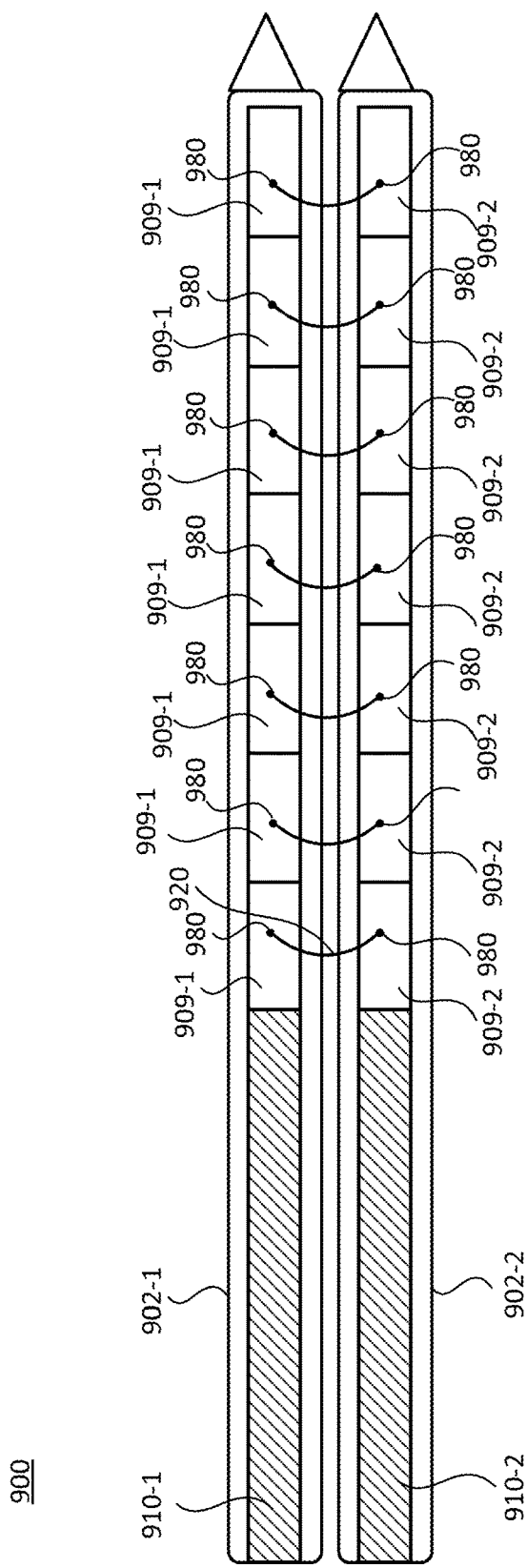
FIG. 9 illustrates a delivery device with two needles loaded with attachment parts.

FIG. 9 illustrates a delivery device 900 having a first needle 902-1 loaded with first attachment parts 909-1 and a second needle 902-1 loaded with second attachment parts 909-2. As shown in FIG. 9, each first attachment part 909-1 is connected to a second attachment part 909-2 via a connecting member 920. The first attachment part 909-1, the second attachment part 909-2, and the connecting member 920 may be any of the attachment parts and connecting members described with reference to the previous figures. The first needle 902-1 and the second needle 902-2 may be disposed side-by-side. The first needle 902-1 may be the same as the second needle 902-2. In other examples, the first needle 902-1 is different than the second needle 902-2. The first and second needles 902-1, 902-2 may be any of the needles described with reference to the previous figures.

However, the first and second needles 902-1, 902-2 may define side openings 980 so that the connecting members 920 can extend out of the first and second needles 902-1, 902-2. The side openings 980 may be defined along an axis of the first needle 902-1, and the side openings 980 may be defined along an axis of the second needle 902-2. Also, the delivery device 900 may include a first pusher 910-1 configured to move the first attachment parts 909-1 through the lumen of the first needle 902-1 and out of the first needle's distal end, and a second pusher 910-2 configured to move the second attachment parts 909-2 through the lumen of the second needle 902-2 and out of the second needle's distal end. In some examples, the first pusher 910-1 and the second pusher 910-2 are configured to be independently operated such that a second attachment part 909-2 can be deployed after a first attachment part 909-1. In other examples, the first pusher 910-1 and the second pusher 910-2 are operated together such that the second attachment part 909-2 is deployed at the same time as the first attachment part 909-1.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An apparatus for delivering attachment devices, the apparatus comprising:
   a needle including a lumen and a distal opening;
   a plurality of attachment devices disposed within the lumen of the needle, each attachment device including a first attachment part and a second attachment part, the first attachment part includes a first end portion and a second end portion, and an extending portion, the extending portion extending from at least one of the first end portion and the second end portion;
   a connecting member coupled to the first attachment part and the second attachment part and configured to attach the first attachment part and second attachment part together, the connecting member being configured to be at least partially housed within at least one of the first attachment part or the second attachment part; and
   an actuator configured to drive each attachment device out of the distal opening of the needle during a surgical procedure.

2. The apparatus of claim 1, wherein the needle includes a shape memory material.

3. The apparatus of claim 1, wherein the connecting member is a suture.

4. The apparatus of claim 1, wherein the actuator is configured to drive the first attachment part to a first location, and the second attachment part to a second location.

5. The apparatus of claim 4, wherein the first location and the second location are located on a same side of a tissue layer.

6. The apparatus of claim 1, wherein the actuator is a pusher wire.

7. The apparatus of claim 1, wherein the first attachment part includes a lumen and a side slot, and the second attachment part includes a lumen and a side slot.

8. The apparatus of claim 1, wherein the plurality of attachment devices are serially disposed within the lumen of the needle.

9. The apparatus of claim 1, wherein each of the first attachment part and the second attachment part includes a coupling member configured to couple an end portion of the connecting member.

10. The apparatus of claim 1, wherein the second attachment part includes at least an extending portion configured to be coupled to the extending portion of the first attachment part.

11. An apparatus for delivering attachment devices, the apparatus comprising:
    a needle carrier;
    a needle configured to move to a first position and a second position in relation to the needle carrier, the needle having a curved portion when in the second position, the needle being substantially linear in the first position, the needle including a lumen and a distal opening;
    a plurality of attachment devices serially disposed within the lumen, each attachment device includes a first attachment part and a second attachment part coupled by a connector member, the first attachment part includes a first part structure and the second attachment part includes a second part structure, the first part structure and the second part structure configured to at least partially contact each other and enclose the connector member within the respective structures; and
    an actuator configured to drive the attachment devices through the lumen and out of the distal opening in either the first position or the second position.

12. The apparatus of claim 11, wherein the needle carrier includes a lumen configured to receive at least one portion of the needle such that the one portion of the needle moves from the first position in which the one portion of the needle is retracted within the needle carrier to the second position in which the one portion of the needle extends from a distal end of the needle carrier.

13. The apparatus of claim 11, wherein the needle includes a shape memory material that is biased to a curved configuration forming the curved portion.

14. The apparatus of claim 11, wherein the curved portion is J-shaped.

15. The apparatus of claim 11, wherein the actuator is a pusher wire, the apparatus further comprising:
    a handle operatively coupled to the pusher wire, wherein manipulation of the handle distally moves the pusher wire to drive the attachment devices towards the distal opening of the needle.

16. A method for delivering attachment devices in a body of a patient, the method comprising:
    loading an attachment device in a lumen of a needle, the attachment device including a first attachment part, a second attachment part, and a connecting member coupled to the first attachment part and the second attachment part;

moving the needle into tissue at an entry point, and moving the needle through the tissue such that the needle curves back to a first location, the first location being located on a same side of tissue as the entry point;

releasing the first attachment part via a distal opening of the needle;

manipulating the needle such that a distal tip of the needle is moved back through the tissue to a second location proximate to the entry point; and releasing the second attachment part via the distal opening of the needle.

17. The method of claim 16, wherein each of the first attachment part and the second attachment part includes a lumen and a reduced-diameter lumen, the connecting member including a first end portion and a second end portion, the connecting member having a first stopper on the first end portion and a second stopper on the second end portion, wherein a diameter of the reduced-diameter lumen is smaller than a diameter of the first stopper or the second stopper.

18. The method of claim 16, wherein the manipulating the needle includes retracting the needle into a needle carrier such that the needle is forced into a linear configuration.

19. The method of claim 16, wherein the tissue is a vaginal wall, and a distal tip of the needle does not completely go through the vaginal wall when moved from the entry point to the first location and moved from the first location to the second location.

* * * * *